(12) United States Patent
Wu et al.

(10) Patent No.: US 11,752,542 B2
(45) Date of Patent: Sep. 12, 2023

(54) METHOD AND SYSTEM FOR ADJUSTING PROCESS PARAMETERS OF DIE-CASTING MACHINE, AND STORAGE MEDIUM

(71) Applicant: CITIC Dicastal Co., Ltd., Qinhuangdao (CN)

(72) Inventors: Yaqi Wu, Qinhuangdao (CN); Xiaobing Huang, Qinhuangdao (CN); Zhiguang Li, Qinhuangdao (CN); Hui Wang, Qinhuangdao (CN); Zuo Xu, Qinhuangdao (CN); Hanqi Wu, Qinhuangdao (CN); Zhihua Zhu, Qinhuangdao (CN); Guoyuan Xiong, Qinhuangdao (CN)

(73) Assignee: CITIC Dicastal Co., Ltd., Qinhuangdao (CN)

( * ) Notice: Subject to any disclaimer, the term of this patent is extended or adjusted under 35 U.S.C. 154(b) by 77 days.

(21) Appl. No.: 17/367,505

(22) Filed: Jul. 5, 2021

(65) Prior Publication Data
US 2022/0143684 A1 May 12, 2022

(30) Foreign Application Priority Data
Nov. 6, 2020 (CN) .......................... 202011227589.0

(51) Int. Cl.
| | |
|---|---|
| B22D 17/32 | (2006.01) |
| B22D 17/20 | (2006.01) |
| B22D 11/18 | (2006.01) |
| B22D 11/00 | (2006.01) |
| B22D 11/06 | (2006.01) |
| B22D 11/22 | (2006.01) |
| C22C 21/00 | (2006.01) |

(52) U.S. Cl.
CPC .......... *B22D 11/187* (2013.01); *B22D 11/003* (2013.01); *B22D 11/0634* (2013.01); *B22D 11/182* (2013.01); *B22D 11/22* (2013.01); *B22D 17/32* (2013.01); *B22D 17/20* (2013.01); *C22C 21/00* (2013.01)

(58) Field of Classification Search
CPC ............................... B22D 17/20; B22D 17/32
USPC ................................... 164/4.1, 150.1, 154.1
See application file for complete search history.

(56) References Cited

U.S. PATENT DOCUMENTS

| | | | |
|---|---|---|---|
| 10,393,720 B2* | 8/2019 | Leblanc | G01N 29/4472 |
| 2008/0308252 A1* | 12/2008 | Kirkman | B22C 9/065 |
| | | | 164/458 |
| 2012/0193060 A1* | 8/2012 | Fulton et al. | B22D 46/00 |
| | | | 164/4.1 |
| 2012/0232685 A1* | 9/2012 | Wang et al. | B22D 46/00 |
| | | | 700/98 |

* cited by examiner

*Primary Examiner* — Kevin P Kerns
(74) *Attorney, Agent, or Firm* — IPRO, PLLC (57) ABSTRACT

Disclosed is a method and system for adjusting process parameters of a die-casting machine, and a storage medium. The method and the system can receive die wheel type, molten aluminum temperature, interruption time and defect information in real time, respond to the above information one by one according to a set response priority order, select die-casting process parameters, and automatically adjust different process parameters for different products and different working conditions, thereby realizing simultaneous control of multiple die-casting machines, replacing manual adjustment and improving product quality stability and production efficiency.

10 Claims, 2 Drawing Sheets

METHOD AND SYSTEM FOR ADJUSTING PROCESS PARAMETERS OF DIE-CASTING MACHINE, AND STORAGE MEDIUM

TECHNICAL FIELD

The present disclosure relates to the technical field of casting equipment, in particular to a method and system for adjusting process parameters of a die-casting machine, and a storage medium.

BACKGROUND

At present, manual adjustment is generally adopted in the field of die-casting machine control. After the abnormal molten aluminum temperature, abnormal interruption time and product appearance problems are found, the process parameters of a die-casting machine are adjusted manually one by one, which results in high work intensity, low adjustment efficiency and unstable product quality.

SUMMARY

The embodiments of the present disclosure provide a method and system for adjusting process parameters of a die-casting machine, and a storage medium. The method and the system can automatically adjust different process parameters for different wheel type products and different working conditions according to molten aluminum temperature information, interruption time information, defect information detected by X-rays and die wheel type information collected in real time in the production process of the die-casting machine, thereby realizing simultaneous control of multiple die-casting machines, replacing manual adjustment and improving product quality stability and production efficiency.

In order to achieve the above purpose, the disclosure provides the following technical solution:

In a first aspect, a method for adjusting process parameters of a die-casting machine is provided, including the following steps: receiving molten aluminum temperature information, interruption time information, die wheel type information and defect information detected by X-rays in real time; setting a priority order from high to low: the die wheel type information, the interruption time information, the defect information detected by X-rays and the molten aluminum temperature information; and responding to the information according to the priority order from high to low one by one, selecting a die-casting process parameter corresponding to the information, and adjusting the process parameters of the die-casting machine according to the selected die-casting process parameter.

In some embodiments, the method includes the steps: responding to the die wheel type information and judging whether a die has been replaced; keeping the die-casting process parameters unchanged if the die has not been replaced; and selecting a die-casting process parameter corresponding to a wheel type of a new die if the die has been replaced.

In some embodiments, the method includes the steps: setting adjustment parameters corresponding to different interruption duration ranges, responding to the interruption time information, and selecting a corresponding adjustment parameter according to an interruption duration range to which the interruption time belongs.

In some embodiments, the interruption duration ranges include: a first interruption duration range [70, 110) sec, a second interruption duration range [110, 180) sec, a third interruption duration range [180, 450) sec, and a fourth interruption duration range [450, 650) sec.

In some embodiments, the method includes the steps: setting adjustment parameters corresponding to X-ray automatic inspection result codes, responding to the defect information detected by X-rays, and selecting a corresponding adjustment parameter according to an obtained X-ray automatic inspection result code.

In some embodiments, the method includes the steps: setting upper and lower limits of molten aluminum temperature, and setting a first adjustment parameter when the molten aluminum temperature is greater than the upper limit, a second adjustment parameter when the molten aluminum temperature is less than the lower limit, and a third adjustment parameter when the molten aluminum temperature is greater than or equal to the lower limit and less than or equal to the upper limit; and responding to the molten aluminum temperature information: selecting the third adjustment parameter when the molten aluminum temperature is greater than or equal to the lower limit and less than or equal to the upper limit, selecting the second adjustment parameter when the molten aluminum temperature is less than the lower limit, and selecting the first adjustment parameter when the molten aluminum temperature is greater than the upper limit.

In some embodiments, the method further includes the steps: responding to a casting die-casting end signal and judging whether set process parameters exist; keeping the process parameters of the die-casting machine unchanged if set process parameters do not exist; and adjusting the process parameters of the die-casting machine according to the set process parameters if set process parameters exist.

In a second aspect, a system for adjusting process parameters of a die-casting machine is provided, including: an information receiving module, used for receiving molten aluminum temperature information, interruption time information, die wheel type information and defect information detected by X-rays in real time; a priority order setting module, used for setting a priority order from high to low: the die wheel type information, the interruption time information, the defect information detected by X-rays and the molten aluminum temperature information; a responding module, used for responding to the information according to the priority order from high to low one by one and selecting a die-casting process parameter corresponding to the information; and a process parameter adjusting module, used for adjusting the process parameters of the die-casting machine according to the selected die-casting process parameter.

In some embodiments, the responding module includes a wheel type information responding module, used for responding to the die wheel type information and judging whether a die has been replaced; keeping the die-casting process parameters unchanged if the die has not been replaced; and selecting a die-casting process parameter corresponding to a wheel type of a new die if the die has been replaced.

In some embodiments, the responding module includes an interruption time responding module, used for setting adjustment parameters corresponding to different interruption duration ranges, responding to the interruption time information, and selecting a corresponding adjustment parameter according to an interruption duration range to which the interruption time belongs.

In some embodiments, the interruption duration ranges include: a first interruption duration range [70, 110) sec, a second interruption duration range [110, 180) sec, a third interruption duration range [180, 450) sec, and a fourth interruption duration range [450, 650) sec.

In some embodiments, the responding module includes a defect information responding module, used for setting adjustment parameters corresponding to X-ray automatic inspection result codes, responding to the defect information detected by X-rays, and selecting a corresponding adjustment parameter according to an obtained X-ray automatic inspection result code.

In some embodiments, the responding module includes a molten aluminum temperature responding module, used for setting upper and lower limits of molten aluminum temperature, and setting a first adjustment parameter when the molten aluminum temperature is greater than the upper limit, a second adjustment parameter when the molten aluminum temperature is less than the lower limit, and a third adjustment parameter when the molten aluminum temperature is greater than or equal to the lower limit and less than or equal to the upper limit; and responding to the molten aluminum temperature information: selecting the third adjustment parameter when the molten aluminum temperature is greater than or equal to the lower limit and less than or equal to the upper limit, selecting the second adjustment parameter when the molten aluminum temperature is less than the lower limit, and selecting the first adjustment parameter when the molten aluminum temperature is greater than the upper limit.

In some embodiments, the responding module includes a die-casting end signal responding module, used for responding to a casting die-casting end signal and judging whether set process parameters exist; keeping the process parameters of the die-casting machine unchanged if set process parameters do not exist; and adjusting the process parameters of the die-casting machine according to the set process parameters if set process parameters exist.

In a third aspect, the embodiments of the present disclosure further provide a storage medium, used for storing non-transitory computer readable instructions, wherein the non-transitory computer readable instructions, when executed, can execute instructions for the method for adjusting the process parameters of the die-casting machine according to any one of the above embodiments.

In a fourth aspect, the embodiments of the present disclosure further provide a system for adjusting process parameters of a die-casting machine, including:
a memory;
a processor; and
one or more computer program modules stored in the memory and configured to be executed by the processor, the one or more computer program modules containing instructions for implementing the method for adjusting process parameters of a die-casting machine according to any one of the above embodiments.

Compared with the prior art, the disclosure has the beneficial effects that:

The disclosure provides a method and system for adjusting process parameters of a die-casting machine, and a storage medium. The method and the system can receive die wheel type, molten aluminum temperature, interruption time and defect information in real time, respond to the above information one by one according to a set response priority order, select die-casting process parameters, and automatically adjust different process parameters for different products and different working conditions, thereby realizing simultaneous control of multiple die-casting machines, replacing manual adjustment and improving product quality stability and production efficiency.

DETAILED DESCRIPTION OF THE EMBODIMENTS

The terms "first", "second", "third" and "fourth" in the description and claims of the present disclosure and the drawings are used to distinguish different objects, but not to describe a specific order. Further, the terms "include" and "have" and any variations thereof are intended to cover non-exclusive inclusion. For example, a process, method, system, product or device including a series of steps or units is not limited to the listed steps or units, but optionally includes steps or units not listed, or optionally further includes other steps or units inherent to the process, method, product or device.

Reference to an "embodiment" herein means that a particular feature, structure or characteristic described in connection with the embodiment may be included in at least one embodiment of the present disclosure. The appearance of this word in various places in the description does not necessarily mean the same embodiment, nor is it an independent or alternative embodiment mutually exclusive with other embodiments. Those skilled in the art understand explicitly and implicitly that the embodiments described herein may be combined with other embodiments.

In order to solve the problems of manual adjustment of process parameters of die-casting machines, such as high work intensity, low adjustment efficiency, and product quality defects and unstable product quality caused by not timely adjustment, the applicant analyzes the reasons for adjustment (including die replacement, interruption time, X-ray results and molten aluminum temperature), formulates corresponding adjustment parameters and adjustment rules under various conditions, and proposes a method and system for adjusting process parameters of a die-casting machine.

An embodiment of the disclosure provides a method for adjusting process parameters of a die-casting machine, including the following steps: receiving molten aluminum temperature information, interruption time information, die wheel type information and defect information detected by X-rays in real time; setting a priority order from high to low: the die wheel type information, the interruption time information, the defect information detected by X-rays and the molten aluminum temperature information; and responding to the information according to the priority order from high to low one by one, selecting a die-casting process parameter corresponding to the information, and adjusting the process parameters of the die-casting machine according to the selected die-casting process parameter.

In some embodiments, the method includes the steps: responding to the die wheel type information and judging whether a die has been replaced; keeping the die-casting process parameters unchanged if the die has not been replaced; and selecting a die-casting process parameter corresponding to a wheel type of a new die if the die has been replaced.

In some embodiments, the method includes the steps: setting adjustment parameters corresponding to different interruption duration ranges, responding to the interruption time information, and selecting a corresponding adjustment parameter according to an interruption duration range to which the interruption time belongs.

In some embodiments, the interruption duration ranges include: a first interruption duration range [70, 110) sec, a second interruption duration range [110, 180) sec, a third interruption duration range [180, 450) sec, and a fourth interruption duration range [450, 650) sec.

In some embodiments, the method includes the steps: setting adjustment parameters corresponding to X-ray automatic inspection result codes, responding to the defect information detected by X-rays, and selecting a corresponding adjustment parameter according to an obtained X-ray automatic inspection result code.

In some embodiments, the method includes the steps: setting upper and lower limits of molten aluminum temperature, and setting a first adjustment parameter when the molten aluminum temperature is greater than the upper limit, a second adjustment parameter when the molten aluminum temperature is less than the lower limit, and a third adjustment parameter when the molten aluminum temperature is greater than or equal to the lower limit and less than or equal to the upper limit; and responding to the molten aluminum temperature information: selecting the third adjustment parameter when the molten aluminum temperature is greater than or equal to the lower limit and less than or equal to the upper limit, selecting the second adjustment parameter when the molten aluminum temperature is less than the lower limit, and selecting the first adjustment parameter when the molten aluminum temperature is greater than the upper limit.

In some embodiments, the method further includes the steps: responding to a casting die-casting end signal and judging whether set process parameters exist; keeping the process parameters of the die-casting machine unchanged if set process parameters do not exist; and adjusting the process parameters of the die-casting machine according to the set process parameters if set process parameters exist.

In a second aspect, another embodiment of the present disclosure provides a system for adjusting process parameters of a die-casting machine, including: an information receiving module, used for receiving molten aluminum temperature information, interruption time information, die wheel type information and defect information detected by X-rays in real time; a priority order setting module, used for setting a priority order from high to low: the die wheel type information, the interruption time information, the defect information detected by X-rays and the molten aluminum temperature information; a responding module, used for responding to the information according to the priority order from high to low one by one and selecting a die-casting process parameter corresponding to the information; and a process parameter adjusting module, used for adjusting the process parameters of the die-casting machine according to the selected die-casting process parameter.

In some embodiments, the responding module includes a wheel type information responding module, used for responding to the die wheel type information and judging whether a die has been replaced; keeping the die-casting process parameters unchanged if the die has not been replaced; and selecting a die-casting process parameter corresponding to a wheel type of a new die if the die has been replaced.

In some embodiments, the responding module includes an interruption time responding module, used for setting adjustment parameters corresponding to different interruption duration ranges, responding to the interruption time information, and selecting a corresponding adjustment parameter according to an interruption duration range to which the interruption time belongs.

In some embodiments, the interruption duration ranges include: a first interruption duration range [70, 110) sec, a second interruption duration range [110, 180) sec, a third interruption duration range [180, 450) sec, and a fourth interruption duration range [450, 650) sec.

In some embodiments, the responding module includes a defect information responding module, used for setting adjustment parameters corresponding to X-ray automatic inspection result codes, responding to the defect information detected by X-rays, and selecting a corresponding adjustment parameter according to an obtained X-ray automatic inspection result code.

In some embodiments, the responding module includes a molten aluminum temperature responding module, used for setting upper and lower limits of molten aluminum temperature, and setting a first adjustment parameter when the molten aluminum temperature is greater than the upper limit, a second adjustment parameters when the molten aluminum temperature is less than the lower limit, and a third adjustment parameter when the molten aluminum temperature is greater than or equal to the lower limit and less than or equal to the upper limit; and responding to the molten aluminum temperature information: selecting the third adjustment parameter when the molten aluminum temperature is greater than or equal to the lower limit and less than or equal to the upper limit, selecting the second adjustment parameter when the molten aluminum temperature is less than the lower limit, and selecting the first adjustment parameter when the molten aluminum temperature is greater than the upper limit.

In some embodiments, the responding module includes a die-casting end signal responding module, used for responding to a casting die-casting end signal and judging whether set process parameters exist; keeping the process parameters of the die-casting machine unchanged if set process parameters do not exist; and adjusting the process parameters of the die-casting machine according to the set process parameters if set process parameters exist.

In a third aspect, the embodiments of the present disclosure further provide a storage medium, used for storing non-transitory computer readable instructions, wherein the non-transitory computer readable instructions, when executed, can execute instructions for the method for adjusting process parameters of a die-casting machine according to any one of the above embodiments.

In a fourth aspect, the embodiments of the present disclosure further provide a system for adjusting process parameters of a die-casting machine, including:

a memory;

a processor; and one or more computer program modules stored in the memory and configured to be executed by the processor, the one or more computer program modules containing instructions for implementing the method for adjusting process parameters of a die-casting machine according to any one of the above embodiments.

The method and system for adjusting the process parameters of the die-casting machine and the storage medium provided in the above embodiments of the present disclosure can make different control strategies for different wheel types according to the changes of parameters of the die-casting machine collected in real time, including the molten aluminum temperature, the interruption time and the X-ray inspection results, and send the control strategies to the die-casting machine in real time (multiple die-casting machines can be controlled simultaneously), so as to achieve real-time control and automatically adjust the process parameters of the die-casting machine, thereby reducing the labor intensity of field operators, improving efficiency and improving the yield.

The technical solution in the embodiments of the present disclosure will be described clearly and completely with reference to the drawings in the embodiments of the present disclosure. Obviously, the described embodiments are part of the embodiments of the present disclosure, not all of them. All other embodiments obtained by those of ordinary skill in the art based on the embodiments in the present disclosure without creative labor fall within the protection scope of the present disclosure.

Embodiment 1

Figure 1:
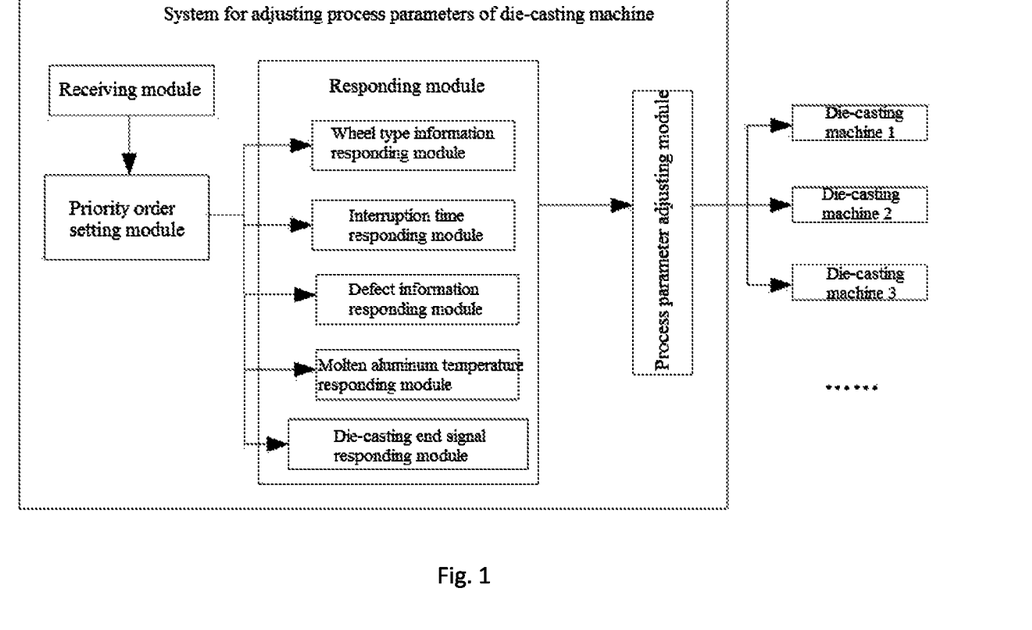
FIG. 1 is a structural schematic diagram of a system for adjusting process parameters of a die-casting machine in the present disclosure.

As shown in FIG. 1, Embodiment 1 provides a system for adjusting process parameters of a die-casting machine, which includes an information receiving module, a priority order setting module, a responding module and a process parameter adjusting module.

The information receiving module is used for receiving molten aluminum temperature information, interruption time information, die wheel type information and defect information detected by X-rays in real time.

The priority order setting module is used for setting a priority order from high to low: the die wheel type information, the interruption time information, the defect information detected by X-rays and the molten aluminum temperature information.

The responding module is used for responding to the information according to the priority order from high to low one by one and selecting a die-casting process parameter corresponding to the information.

The process parameter adjusting module is used for adjusting the process parameters of the die-casting machine according to the selected die-casting process parameter.

The responding module includes a wheel type information responding module, an interruption time responding module, a defect information responding module, a molten aluminum temperature responding module and a die-casting end signal responding module.

The wheel type information responding module is used for responding to the die wheel type information and judging whether a die has been replaced; keeping the die-casting process parameters unchanged if the die has not been replaced; and selecting a die-casting process parameter corresponding to a wheel type of a new die if the die has been replaced.

The interruption time responding module is used for setting adjustment parameters corresponding to different interruption duration ranges, responding to the interruption time information, and selecting a corresponding adjustment parameter according to an interruption duration range to which the interruption time belongs. The interruption duration ranges include: a first interruption duration range [70, 110) sec, a second interruption duration range [110, 180) sec, a third interruption duration range [180, 450) sec, and a fourth interruption duration range [450, 650) sec.

The defect information responding module is used for setting adjustment parameters corresponding to X-ray automatic inspection result codes, responding to the defect information detected by X-rays, and selecting a corresponding adjustment parameter according to an obtained X-ray automatic inspection result code.

The molten aluminum temperature responding module is used for setting upper and lower limits of molten aluminum temperature, and setting a first adjustment parameter when the molten aluminum temperature is greater than the upper limit, a second adjustment parameter when the molten aluminum temperature is less than the lower limit, and a third adjustment parameter when the molten aluminum temperature is greater than or equal to the lower limit and less than or equal to the upper limit; and responding to the molten aluminum temperature information: selecting the third adjustment parameter when the molten aluminum temperature is greater than or equal to the lower limit and less than or equal to the upper limit, selecting the second adjustment parameter when the molten aluminum temperature is less than the lower limit, and selecting the first adjustment parameter when the molten aluminum temperature is greater than the upper limit.

The die-casting end signal responding module is used for responding to a casting die-casting end signal and judging whether set process parameters exist; keeping the process parameters of the die-casting machine unchanged if set process parameters do not exist; and adjusting the process parameters of the die-casting machine according to the set process parameters if set process parameters exist.

Figure 2:
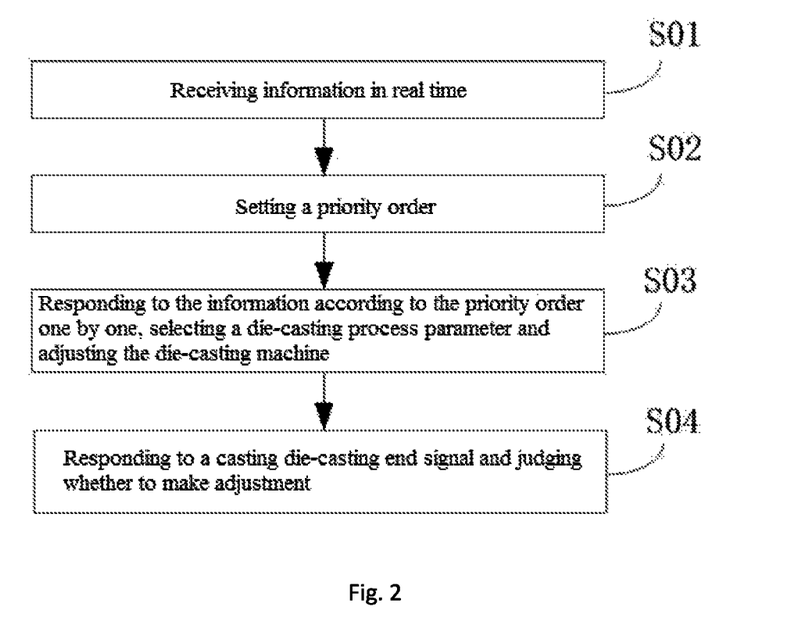
FIG. 2 is a first flow chart of a method for adjusting process parameters of a die-casting machine in the present disclosure.

FIG. 2 is a flow chart of an adjustment method of a system for adjusting process parameters of a die-casting machine. The method for adjusting the process parameters of the die-casting machine includes the following steps:

S01: receiving molten aluminum temperature information, interruption time information, die wheel type information and defect information detected by X-rays in real time;

S02: setting a priority order from high to low: the die wheel type information, the interruption time information, the defect information detected by X-rays and the molten aluminum temperature information; and S03: responding to the information according to the priority order from high to low one by one, selecting a die-casting process parameter corresponding to the information, and adjusting the process parameters of the die-casting machine according to the selected die-casting process parameter.

Wherein, S03 includes the steps: responding to the die wheel type information and judging whether a die has been replaced; keeping the die-casting process parameters unchanged if the die has not been replaced; and selecting a die-casting process parameter corresponding to a wheel type of a new die if the die has been replaced.

Wherein, S03 includes the steps: setting adjustment parameters corresponding to different interruption duration ranges, responding to the interruption time information, and selecting a corresponding adjustment parameter according to an interruption duration range to which the interruption time belongs.

Wherein, S03 includes the steps: setting adjustment parameters corresponding to X-ray automatic inspection result codes, responding to the defect information detected by X-rays, and selecting a corresponding adjustment parameter according to an obtained X-ray automatic inspection result code.

Wherein, S03 includes the steps: setting upper and lower limits of molten aluminum temperature, and setting a first adjustment parameter when the molten aluminum temperature is greater than the upper limit, a second adjustment parameter when the molten aluminum temperature is less than the lower limit, and a third adjustment parameter when the molten aluminum temperature is greater than or equal to the lower limit and less than or equal to the upper limit; and responding to the molten aluminum temperature information: selecting the third adjustment parameter when the molten aluminum temperature is greater than or equal to the lower limit and less than or equal to the upper limit, selecting the second adjustment parameter when the molten aluminum temperature is less than the lower limit, and selecting the first adjustment parameter when the molten aluminum temperature is greater than the upper limit.

At the end of die-casting of each casting, the method further includes S04: responding to a casting die-casting end signal and judging whether set process parameters exist; keeping the process parameters of the die-casting machine unchanged if set process parameters do not exist; and adjusting the process parameters of the die-casting machine according to the set process parameters if set process parameters exist. Because the die-casting end signal is generated outside the die-casting process and does not conflict with the molten aluminum temperature information, the interruption time information, the die wheel type information and the defect information detected by X-rays, the die-casting end signal does not participate in the setting of a priority order.

Figure 3:
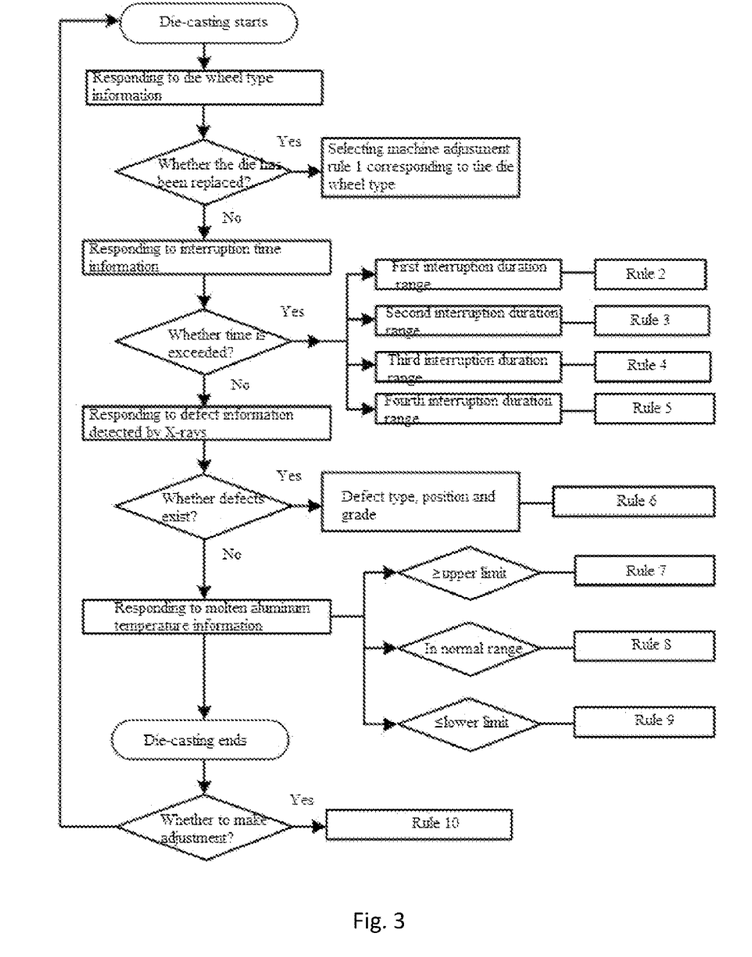
FIG. 3 is a second detailed flow chart of a method for adjusting process parameters of a die-casting machine in the present disclosure.

FIG. 3 is a detailed flow chart of an adjustment method of a system for adjusting process parameters of a die-casting machine in Embodiment 1. After the die-casting machine starts to work, the molten aluminum temperature information, the interruption time information, the die wheel type information and the defect information detected by X-rays are received in real time, and a priority order is set from high to low: the die wheel type information, the interruption time information, the defect information detected by X-rays and the molten aluminum temperature information, that is, adjustment is carried out according to the rule corresponding to a wheel type after die change first, then whether the interruption time is abnormal is judged, after the abnormal interruption time is adjusted, then adjustment is carried out according to the X-ray inspection result, and then whether the molten aluminum temperature is abnormal is judged.

(1) Responding to the die wheel type information: when a die of the die-casting machine is changed, different die-casting process parameters are selected and adjusted according to corresponding different wheel types of the die. For example, the adjustment process is as follows: when the change of the die of the die-casting machine is monitored, a die model to be used, such as 00218C02-1, is obtained; a machine adjustment rule 1 corresponding to the wheel type of the die is selected; and the machine adjustment rule 1 is obtained according to the die model: the dwell time is set to be 1 sec and all the cooling channels are closed at the beginning of die-casting of a first hub after die change, the dwell time is set to be 80 sec and cooling time 60 sec and only a first, a second and a third cooling channels are closed at the beginning of die-casting of a second hub, and the dwell time, cooling time and cooling channels are restored to the original process at the beginning of die-casting of a third hub.

(2) Responding to the interruption time information: in the interruption time adjustment process, different adjustment rules are obtained according to different interruption time ranges (the first interruption duration range, the second interruption duration range, the third interruption duration range and the fourth interruption duration range), so as to adjust the process parameters. The interruption duration is the duration from the end of die-casting of one hub to the beginning of die-casting of the next hub, and belongs to the continuous production process of a single die.

For example, for the wheel type 00218C02-1, the four interruption duration ranges are set as [70, 110) sec, [110, 180) sec, [180,450) sec and [450,650) sec respectively. When the interruption time is monitored to be within one of these four ranges, the die-casting process parameters are adjusted according to the corresponding rules. When the interruption time is within the first interruption duration range, a rule 2 is that the dwell time is reduced by 5 sec and the first and the second cooling channels are closed during die-casting of the first hub after the interruption time, and the original process is restored for the second and subsequent hubs. When the interruption time is within the second interruption duration range, a rule 3 is that the dwell time is set to be 100 sec and cooling time 60 sec and the first, the second and the third cooling channels are closed during die-casting of the first hub after the interruption time, and the original process is restored for the second and subsequent hubs. When the interruption time is within the third interruption duration range, a rule 4 is that the dwell time is set to be 1 sec and cooling channels are all closed during die-casting of the first hub after the interruption time, the dwell time is set to be 80 sec and cooling time 70 sec and only the first, the second and the third cooling channels are closed during die-casting of the second hub, and the original process is restored for the third and subsequent hubs. When the interruption time is within the fourth interruption duration range, a rule 5 is that the adjustment rules of the first two hubs after the interruption time are the same as the rule 4, the third hub is not adjusted, and the original process is restored for the fourth hub.

If the interruption duration does not exceed the set time, for example, less than 70 sec, no adjustment shall be made. If the interruption duration exceeds the set maximum interruption time, for example, more than 650 sec, no automatic adjustment shall be made, and manual adjustment shall be made by field operators.

(3) Responding to the defect information detected by X-rays: adjustment is made according to X-ray results, different adjustment rules are adopted according to quality defect results detected by X-rays, including different defect types, defect positions and defect grades, and the process parameters of the die-casting machine are automatically controlled accordingly.

In Embodiment 1, the X-ray automatic inspection result code is automatically acquired in real time. If the wheel type 00218C02-1 has the first-grade defect of spoke root shrinkage, then the code is 10311, and adjustment is made according to an X-ray adjustment rule corresponding to defect 10311. Rule 6: after die-casting of the first hub starts, the opening time of a fourth and the third cooling channels increases by 5 sec, the working time decreases by 5 sec, and for the second hub, the opening time of the fourth cooling channel increases by 5 sec, and the working time decreases by 5 sec.

(4) Responding to the molten aluminum temperature information: adjustment is made according to the molten aluminum temperature. When the molten aluminum temperature exceeds the upper limit or lower limit, the process parameters are adjusted. When the molten aluminum temperature returns to the normal range, the process parameters are also adjusted to the original process values.

For example, the upper limit of the molten aluminum temperature is set to be 706 DEG C. and the lower limit 695 DEG C.. When the molten aluminum temperature is higher than the upper limit 706 DEG C., a first adjustment parameter, i.e., rule 7, is that the dwell time increases by 5 sec, and when the temperature returns to the normal range of 698 to 704 DEG C., the dwell time is restored to the original process. When the molten aluminum temperature is lower than the lower limit 695 DEG C., a second adjustment parameter, i.e., rule 9, is that the dwell time is reduced by 5 sec. When the molten aluminum temperature is greater than or equal to the lower limit value and less than or equal to the upper limit value, a third adjustment parameter, i.e., rule 8 is that the dwell time is restored to the original process (different wheel types have different dwell time ranges, and the operator will set a standard process as the original process according to the actual situation on site, and the dwell time range of the original process is generally 110 sec to 210 sec).

(5) Responding to the casting die-casting end signal: every hub judges whether a rule 10 exists for the wheel type when die-casting ends, that is, whether adjustment is needed when die-casting ends, if the rule 10 exists, adjustment is made, and if the rule 10 does not exist, adjustment is not needed. For example, if the rule 10 is that a fifth cooling channel is closed when die-casting ends for the first hub, adjustment is made accordingly.

The method and system for adjusting the process parameters of the die-casting machine provided in Embodiment 1 can make different control strategies for different wheel types according to the changes of parameters of the die-casting machine collected in real time, including the molten aluminum temperature, the interruption time and the X-ray inspection results, and send the control strategies to the die-casting machine in real time (multiple die-casting machines can be controlled simultaneously), so as to achieve real-time control and automatically adjust the process parameters of the die-casting machine, thereby reducing the labor intensity of field operators, improving efficiency and improving the yield.

Embodiment 2

Embodiment 2 provides a storage medium used for storing non-transitory computer-readable instructions, wherein the non-transitory computer-readable instructions, when executed, can execute instructions for the method for adjusting the process parameters of the die-casting machine according to any one of the above embodiments. By means of the storage medium, for example, in a system for adjusting process parameters of a die-casting machine, when the stored non-transitory computer readable instructions are executed by a computer, the following can be realized: receiving molten aluminum temperature information, interruption time information, die wheel type information and defect information detected by X-rays in real time; setting a priority order from high to low: the die wheel type information, the interruption time information, the defect information detected by X-rays and the molten aluminum temperature information; responding to the information according to the priority order from high to low one by one, selecting a die-casting process parameter corresponding to the information, and adjusting the process parameters of the die-casting machine according to the selected die-casting process parameter; at the end of die-casting of each casting, responding to a casting die-casting end signal and judging whether set process parameters exist; keeping the process parameters of the die-casting machine unchanged if set process parameters do not exist; and adjusting the process parameters of the die-casting machine according to the set process parameters if set process parameters exist.

The storage medium may be various forms of computer-readable storage media, such as volatile memory and/or nonvolatile memory. The volatile memory may be, for example, random access memory (RAM) and/or cache. The nonvolatile memory may be, for example, read-only memory (ROM), hard disk, erasable programmable read-only memory (EPROM), portable compact disk read-only memory (CD-ROM), USB memory, and flash memory. One or more computer program modules can be stored on the computer readable storage medium, and a processor can run one or more computer program modules to realize real-time adjustment of die-casting process parameters of a plurality of die-casting machines. The computer-readable storage medium can also store various applications and various data as well as various data used and/or generated by the applications. In some embodiments, the memory medium can be set on a server side (or the cloud), for example, the non-transitory computer readable instructions can be stored in the cloud or cloud disk.

Embodiment 3

Figure 4:
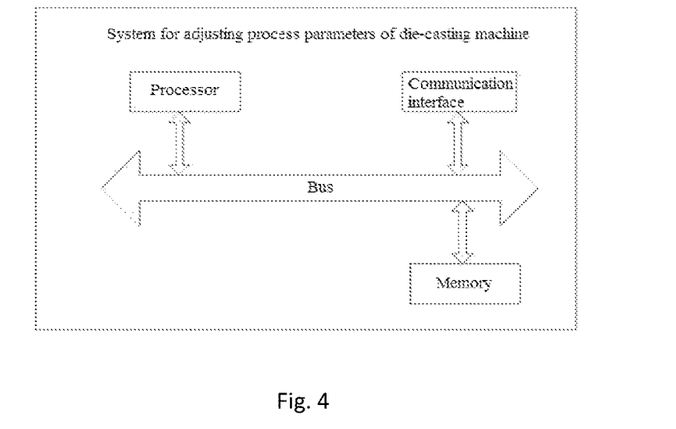
FIG. 4 is a structural schematic diagram of a system for adjusting process parameters of a die-casting machine in the present disclosure.

As shown in FIG. 4, an embodiment of the present disclosure also provides a system for adjusting process parameters of a die-casting machine, which includes a memory, a processor, a communication interface and one or more computer program modules. The one or more computer program modules are stored in the memory and are configured to be executed by the processor, and the one or more computer program modules include instructions for implementing the method for adjusting the process parameters of the die-casting machine according to any one of the above embodiments. The processor is in signal connection with the memory and the communication interface, and the memory, the processor and the communication interface may be interconnected through a bus system and/or other forms of connection mechanisms (not shown).

The processor is used for running non-transitory computer readable instructions, and when the non-transitory computer readable instructions, when run by the processor, can execute one or more steps of the method for adjusting the process parameters of the die-casting machine according to any one of the above embodiments. For example, the processor may be a central processing unit (CPU), a digital signal processor (DSP) or other processing units with data processing capability and/or program execution capability, such as a field programmable gate array (FPGA). For example, the CPU may be X86 or ARM architecture, etc. The processor may be a general-purpose processor or a special-purpose processor, and can control the modules in the system for adjusting process parameters of a die-casting machine to perform the desired functions.

The memory is used to store non-transitory computer readable instructions (one or more computer program modules). For example, the memory may include any combination of one or more computer program products, which may include various forms of computer-readable storage media, such as volatile memory and/or nonvolatile memory. The volatile memory may be, for example, random access memory (RAM) and/or cache. The nonvolatile memory may be, for example, read-only memory (ROM), hard disk, erasable programmable read-only memory (EPROM), portable compact disk read-only memory (CD-ROM), USB memory, and flash memory. One or more computer program modules can be stored on the computer readable storage medium, and the processor can run one or more computer program modules to realize adjustment of process parameters of a plurality of die-casting machines. The computer-readable storage medium can also store various applications and various data as well as various data used and/or generated by the applications.

In some embodiments, the memory and the processor may also be set on a server side (or the cloud), for example, one or more computer program modules may be stored in the cloud or cloud disk.

The communication interface is connected with the system for adjusting process parameters of a die-casting machine and at least one die-casting machine for receiving and issuing information. In some embodiments, based on a corresponding communication protocol, the molten aluminum temperature information, the interruption time information, the die wheel type information, the defect information detected by X-rays and the casting die-casting end signal reported by at least one die-casting machine can be received through the communication interface (such as wired local area network, wireless local area network, 3G/4G/5G communication network, Bluetooth, etc.), various signals can be responded to and appropriate rules (or process parameters) can be selected and sent to various die-casting machines to complete the adjustment of the process parameters of the die-casting machines. For example, the communication protocol may be any suitable communication protocol such as Bluetooth communication protocol, Ethernet, serial interface communication protocol and parallel interface communication protocol, which is not limited by embodiments of the present disclosure.

What is claimed is:

1. A method of a die-casting machine, comprising the following steps:
   receiving molten aluminum temperature information, interruption time information, die wheel type information and defect information detected by X-rays in real time;
   setting a priority order from high to low: the die wheel type information, the interruption time information, the defect information detected by X-rays and the molten aluminum temperature information;
   responding to the information according to the priority order from high to low one by one, selecting a die-casting process parameter corresponding to the information, and adjusting the process parameters of the die-casting machine according to the selected die-casting process parameter, wherein judging whether a die has been replaced in response to the die wheel type information; keeping the die-casting process parameters unchanged under the condition that the die has not been replaced; and selecting a die-casting process parameter corresponding to a wheel type of a new die under the condition that the die has been replaced; and wherein setting an upper limit and a lower limit of molten aluminum temperature, and setting a first adjustment parameter when the molten aluminum temperature is greater than the upper limit, a second adjustment parameter when the molten aluminum temperature is less than the lower limit, and a third adjustment parameter when the molten aluminum temperature is greater than or equal to the lower limit and less than or equal to the upper limit; and responding to the molten aluminum temperature information: selecting the third adjustment parameter when the molten aluminum temperature is greater than or equal to the lower limit and less than or equal to the upper limit, selecting the second adjustment parameter when the molten aluminum temperature is less than the lower limit, and selecting the first adjustment parameter when the molten aluminum temperature is greater than the upper limit; and
   performing a die-casting process by the die-casting machine based on the adjusted process parameters.

2. The method of a die-casting machine according to claim 1, comprising the steps: setting adjustment parameters corresponding to different interruption duration ranges, responding to the interruption time information, and selecting a corresponding adjustment parameter according to an interruption duration range to which the interruption time belongs.

3. The method of a die-casting machine according to claim 2, wherein the interruption duration ranges comprise:
   a first interruption duration range [70, 110) sec,
   a second interruption duration range [110, 180) sec,
   a third interruption duration range [180, 450) sec, and
   a fourth interruption duration range [450, 650) sec.

4. The method of a die-casting machine according to claim 1, comprising the steps: setting adjustment parameters corresponding to X-ray automatic inspection result codes, responding to the defect information detected by X-rays, and selecting a corresponding adjustment parameter according to an obtained X-ray automatic inspection result code.

5. The method of a die-casting machine according to claim 1, comprising the steps: responding to a casting die-casting end signal and judging whether set process parameters exist; keeping the process parameters of the die-casting machine unchanged under the condition that set process parameters do not exist; and adjusting the process parameters of the die-casting machine according to the set process parameters under the condition that set process parameters exist.

6. A die-casting machine, comprising:
   an information receiving module, configured to receive molten aluminum temperature information, interruption time information, die wheel type information and defect information detected by X-rays in real time;
   a priority order setting module, configured to set a priority order from high to low: the die wheel type information, the interruption time information, the defect information detected by X-rays and the molten aluminum temperature information;
   a responding module, configured to respond to the information according to the priority order from high to low one by one and select a die-casting process parameter corresponding to the information; and
   a process parameter adjusting module, configured to adjust the process parameters of the die-casting machine according to the selected die-casting process parameter,
   wherein the die-casting machine performs a die-casting process based on the adjusted process parameters,
   wherein the responding module comprises a wheel type information responding module, configured to judge whether a die has been replaced in response to the die wheel type information; keep the die-casting process parameters unchanged under the condition that the die has not been replaced; and select a die-casting process parameter corresponding to a wheel type of a new die under the condition that the die has been replaced,
   wherein the responding module comprises a molten aluminum temperature responding module, configured to set an upper limit and a lower limit of molten aluminum temperature, and set a first adjustment parameter when the molten aluminum temperature is greater than the upper limit, a second adjustment parameter when the molten aluminum temperature is less than the lower limit, and a third adjustment parameter when the molten aluminum temperature is greater than or equal to the lower limit and less than or equal to the upper limit; and respond to the molten aluminum temperature information: selecting the third adjustment parameter when the molten aluminum temperature is greater than or equal to the lower limit and less than or equal to the upper limit, selecting the second adjustment parameter when the molten aluminum temperature is less than the lower limit, and selecting the first adjustment parameter when the molten aluminum temperature is greater than the upper limit.

7. The die-casting machine according to claim 6, wherein the responding module comprises an interruption time responding module, configured to set adjustment parameters corresponding to different interruption duration ranges, respond to the interruption time information, and select a corresponding adjustment parameter according to an interruption duration range to which the interruption time belongs.

8. The die-casting machine according to claim 7, wherein the interruption duration ranges comprise:
   a first interruption duration range [70, 110) sec,
   a second interruption duration range [110, 180) sec,
   a third interruption duration range [180, 450) sec, and
   a fourth interruption duration range [450, 650) sec.

9. The die-casting machine according to claim 6, wherein the responding module comprises a defect information responding module, configured to set adjustment parameters corresponding to X-ray automatic inspection result codes, respond to the defect information detected by X-rays, and select a corresponding adjustment parameter according to an obtained X-ray automatic inspection result code.

10. The die-casting machine according to claim 6, wherein the responding module comprises a die-casting end signal responding module, configured to respond to a casting die-casting end signal and judge whether set process parameters exist; keep the process parameters of the die-casting machine unchanged under the condition that set process parameters do not exist; and adjust the process parameters of the die-casting machine according to the set process parameters under the condition that set process parameters exist.

* * * * *